United States Patent
Cloutier et al.

(10) Patent No.: US 8,518,259 B2
(45) Date of Patent: Aug. 27, 2013

(54) DE-AIRING OXYGENATOR FOR TREATING BLOOD IN AN EXTRACORPOREAL BLOOD CIRCUIT

(75) Inventors: Patrick Cloutier, Andover, MN (US); Robert Olsen, Plymouth, MN (US); Stephen Roller, Minneapolis, MN (US); Chris Plott, St. Paul, MN (US); Al McLevish, Apple Valley, MN (US); Ming Li, Roseville, MN (US); Michael Laxen, Minneapolis, MN (US); John Knoll, Brooklyn Park, MN (US); Gregory Hake, Otsego, MN (US)

(73) Assignee: Medtronic, Inc., Minneapolis, MN (US)

( * ) Notice: Subject to any disclaimer, the term of this patent is extended or adjusted under 35 U.S.C. 154(b) by 344 days.

(21) Appl. No.: 13/015,363

(22) Filed: Jan. 27, 2011

(65) Prior Publication Data

US 2012/0193289 A1    Aug. 2, 2012

(51) Int. Cl.
   *B01D 61/30* (2006.01)
   *B01D 61/28* (2006.01)
   *B01D 61/20* (2006.01)
   *B01D 61/18* (2006.01)
   *A61M 1/36* (2006.01)

(52) U.S. Cl.
   USPC ........... 210/646; 210/175; 210/180; 210/183; 210/184; 210/188; 210/252; 210/256; 210/258; 210/436; 210/472; 210/650; 422/44; 422/45; 422/46; 422/47; 422/48; 604/4.01; 604/5.01; 604/6.09; 604/6.13; 604/6.14; 604/28

(58) Field of Classification Search
   USPC ................. 210/175, 180, 183, 184, 188, 252, 210/256, 258, 436, 472, 646, 650; 422/44, 422/45, 46, 47, 48; 604/4.01, 5.01, 6.09, 604/6.13, 6.14, 28
   See application file for complete search history.

(56) References Cited

U.S. PATENT DOCUMENTS

| | | | |
|---|---|---|---|
| 3,771,290 | A | 11/1973 | Stethem |
| 4,344,777 | A | 8/1982 | Siposs |
| 4,368,118 | A | 1/1983 | Siposs |
| 4,684,508 | A | 8/1987 | Sutherland |
| 4,698,207 | A | 10/1987 | Bringham et al. |
| 4,876,066 | A | 10/1989 | Bringham et al. |

(Continued)

FOREIGN PATENT DOCUMENTS

| | | |
|---|---|---|
| EP | 0264696 | 4/1988 |
| EP | 0378168 | 7/1990 |

OTHER PUBLICATIONS

Sueda et al. "Development of an Outside Flow membrane Oxygenator Using a Silicone Hollow Fiber" ASAIO Journal 1993, 39 Jul./Sep. 1993, No. 3, pp. M457-M460.

*Primary Examiner* — John Kim (57) ABSTRACT

An apparatus for de-aering, oxygenating and controlling a temperature of blood in an extracorporeal blood circuit. The apparatus includes a housing, a manifold body, a heat exchanger, and an oxygenator. A blood inlet tangentially directs blood into a first chamber of the housing. The manifold body is disposed in a second chamber, and includes a core and a plurality of vanes that define channels. The heat exchanger is arranged around the manifold body, and the oxygenator around the heat exchanger. The channels are open to the heat exchanger. An established blood flow path includes rotational flow within the first chamber to separate air from the blood, generally longitudinal flow from the first chamber and along the channels, and generally radial flow through the heat exchanger and the oxygenator. With this construction, gross air removal occurs prior to the blood passing through the heat exchanger and oxygenator.

24 Claims, 10 Drawing Sheets

(56) References Cited

U.S. PATENT DOCUMENTS

| | | |
|---|---|---|
| 4,975,247 A | 12/1990 | Badolato et al. |
| 5,270,004 A | 12/1993 | Cosentino et al. |
| 5,376,263 A | 12/1994 | Fischel |
| 5,632,894 A | 5/1997 | White et al. |
| 5,817,279 A | 10/1998 | Eilers et al. |
| 6,053,967 A | 4/2000 | Heilmann et al. |
| 6,398,955 B1 | 6/2002 | Fumiyama et al. |
| 6,998,093 B1 | 2/2006 | McIntosh et al. |
| 7,798,985 B2 | 9/2010 | Engelhardt et al. |
| 2002/0110485 A1 | 8/2002 | Stringer et al. |
| 2007/0258856 A1 | 11/2007 | Oslen et al. |
| 2009/0105630 A1 | 4/2009 | Huang et al. |
| 2010/0274170 A1 | 10/2010 | Carpenter et al. |

DE-AIRING OXYGENATOR FOR TREATING BLOOD IN AN EXTRACORPOREAL BLOOD CIRCUIT

BACKGROUND

The present disclosure relates to extracorporeal blood circuit devices, and related methods of use. More particularly, it relates to devices for de-aering and oxygenating blood in an extracorporeal blood circuit, along with other possible treatments such as temperature control.

An extracorporeal blood circuit is commonly used during cardiopulmonary bypass to withdraw blood from the venous portion of the patient's circulation system (via a venous cannula) and return the blood to the arterial portion (via an arterial cannula). The extracorporeal blood circuit typically includes a venous drainage line, a venous blood reservoir, a blood pump, an oxygenator, a heat exchanger, one or more filters, and blood transporting tubing, ports, and connection pieces interconnecting the components.

Blood oxygenators are disposable components of extracorporeal circuits and are used to oxygenate blood. In general terms, the oxygenator takes over, either partially or completely, the normal gas exchange function of the patient's lungs. The oxygenator conventionally employs a microporous membrane or bundle comprised of thousands of microporous or semipermeable hollow fibers. Blood flow is directed around the outside surfaces of hollow fibers. Concurrently, an oxygen-rich gas mixture is passed through the fiber lumens. Due to the relatively high concentration of carbon dioxide in the blood arriving from the patient, carbon dioxide is transferred from the blood, diffusing across the microporous fibers and into the passing stream of oxygenating gas. At the same time, oxygen is transferred from the oxygenating gas, diffusing across the fibers and into the blood. The oxygen content of the blood is thereby raised, and the carbon dioxide content is reduced.

Typically, the patient's blood is continuously pumped through the heat exchanger component prior to interfacing with the oxygenator. The heat exchanger core is generally made of a metal or plastic that is able to transfer heat effectively to blood coming into contact with the metal or plastic. With extracorporeal blood circuit applications, the heat exchanger core is normally formed by a series or bundle of capillary tubes. A suitable heat transfer fluid, such as water, is pumped through the heat exchanger core, separate from the blood but in heat transfer relationship therewith. The water is either heated or cooled externally of the heat exchanger, with the heat exchanger functioning to control or adjust a temperature of the blood in a desired direction. After contacting the heat exchanger core, the blood then typically flows to the oxygenator. In fact, many commercially available oxygenator devices integrate a heat exchanger core with a membrane-type oxygenator. With these integrated, combination devices, the oxygenator membrane bundle can be disposed directly over the heat exchanger core's capillary tubes.

Conventionally, the filter device (e.g., an arterial filter) is fluidly connected within the extracorporeal circuit downstream from (or upstream of) the oxygenator, and operates to remove gross air (e.g., air bubbles) and particles on the order of 20-40 microns, as well as trap gaseous microemboli (GME). Known arterial blood filters are available from Medtronic, Inc. under the trade name Affinity® Arterial Filter, and incorporate a membrane or screen filter media with a sufficiently small porosity for capturing GME. The oxygenator and arterial filter devices normally are physically separated components or devices of the circuit.

While implementation of the separate oxygenator and arterial filter devices as part of an extracorporeal blood circuit is well accepted, certain concerns may arise. An arterial filter typically adds 200 mL (or more) of prime volume to the extracorporeal blood circuit; this added prime volume is undesirable as it can lead to increased hemodilution of the patient. As a point of reference, in practice, it is necessary to initially fill the venous and arterial cannulae with the patient's blood and to prime (i.e., completely fill) the extracorporeal blood circuit with a biocompatible prime solution before the arterial line and the venous return lines are coupled to the blood filled cannulae inserted into the patient's arterial and venous systems, respectively. The volume of blood and/or prime solution liquid that is pumped into the extracorporeal blood circuit to "prime" is referred to as the "prime volume". Typically, the extracorporeal blood circuit is first flushed with $CO_2$ prior to priming. The priming flushes out any extraneous $CO_2$ gas from the extracorporeal blood circuit prior to the introduction of the patient's blood. The larger the prime volume, the greater the amount of prime solution present in the extracorporeal blood circuit that otherwise mixes with the patient's blood. The mixing of the blood and prime solution may cause hemodilution that is disadvantageous and undesirable because the relative concentration of red blood cells must be maintained during the surgical procedure in order to minimize adverse effects to the patient. It is therefore desirable to minimize the extracorporeal blood circuit's prime volume (and thus the required volume of prime solution).

Devices have been proposed that combine or integrate the arterial filter with the oxygenator. Many of these combination-type devices remove air and particles either post-oxygenation phase or integral with the oxygenation phase (e.g., an arterial filter media disposed within a thickness of the oxygenator's wound hollow fiber bundle). In some instances, this may be less than optimal. For example, directing macro air-containing blood through a GME-type filter media during or after the oxygenation phase could allow for the gross or macro air to be "chopped" up into micro air, possibly increasing an amount of the more difficult to remove gaseous microemboli.

With other oxygenator device designs, incoming blood flow is compressed to separate gas from the blood prior to oxygenation. Yet others pass the blood flow through a tortuous path via multiple windows and channels. These approaches may also be problematic. The cells (e.g., red blood cells, white blood cells, platelets) in human blood are delicate and can be traumatized if subjected to shear forces. Therefore, the blood flow velocity inside the oxygenator (as well as other components of the extracorporeal blood circuit) must not be excessive. The configuration in geometry, along with required velocities of the blood, makes some de-aering and oxygenation devices traumatic to the blood and thus unsafe. In addition, the devices may create re-circulations (eddies) or stagnant areas that can lead to clotting. Thus, the configuration and geometry of the various circuit components for a blood flow path is desired to not create re-circulations (eddies) or stagnant areas that can lead to blood clot production.

In light of the above, a need exists for an extracorporeal blood circuit oxygenator device that that combines the attributes of a filter with an oxygenator by affecting de-aering of the blood prior to the oxygenating phase and by filtering particulate, with minimal pressure drop and exposure to shear forces.

SUMMARY

Some aspects in accordance with principles of the present disclosure relate to an apparatus for de-aering, oxygenating and controlling a temperature of blood in an extracorporeal blood circuit. The apparatus includes a housing, a blood inlet, a manifold body, a heat exchanger, an oxygenator, and a blood outlet. The housing generally defines a first chamber and a second chamber. The first chamber is fluidly open to the second chamber. The blood inlet is fluidly open to the first chamber and arranged relative to a side wall thereof so as to direct incoming blood tangentially into the first chamber. The manifold body is disposed in the second chamber, and includes a central core and a plurality of vanes. The core forms a head. The vanes project from an outer surface of the core to define a plurality of channels. The manifold body is arranged within the housing such that the head is aligned with the first chamber. The heat exchanger includes a plurality of heat transfer elements arranged around the manifold body. Upon final assembly, the channels are open to the heat exchanger. The oxygenator includes a plurality of gas exchange elements arranged around the heat exchanger. The blood outlet is fluidly open to the second chamber. With this construction, the apparatus establishes a blood flow path from the blood inlet to the blood outlet. The blood flow path includes rotational flow within the first chamber to separate air from the blood, generally longitudinal flow from the first chamber and along the channels, and generally radial flow from the channels, through the heat exchanger and the oxygenator, and to the outlet. In some embodiments, a top surface of the head is longitudinally spaced from the blood inlet, and establishes a de-aering region within the first chamber at which the rotational flow is established. In this regard, the top surface is longitudinally below the blood inlet. In other embodiments, the side wall of the first chamber has a uniform diameter such that blood flow from the first chamber is not compressed. In yet other embodiments, the apparatus further includes a filter media within the second chamber and along the blood flow path. With this construction, gross air removal occurs in the first chamber, prior to the blood flow passing through the heat exchanger, oxygenator, and filter medium.

Yet other aspects in accordance with principles of the present disclosure relate to an apparatus for de-aering, oxygenating and controlling a temperature of blood in an extracorporeal blood circuit. The apparatus includes a housing, manifold body, a blood inlet, a heat exchanger, and oxygenator, and a blood outlet. The housing defines a central axis. The manifold body is disposed within the housing and is arranged co-axial with the central axis. The manifold body includes a core. Further, the housing and the manifold body combine to define a de-aering region having a cylindrical side wall and bounded along the central axis by a top wall and a low pressure support surface opposite the top wall. The blood inlet is fluidly open to the de-aering region and arranged relative to the side wall to direct incoming blood tangentially into the de-aering region. In this regard, the low pressure support surface is longitudinally offset from the blood inlet such that a vortex flow induced into the incoming blood at the de-aering region is established on the low pressure support surface. The heat exchanger is disposed within the housing and includes a plurality of heat transfer elements arranged around the manifold body. The oxygenator is also disposed within the housing and includes a plurality of gas exchange elements arranged around the heat exchanger. Finally, the blood outlet is fluidly open to an interior of the housing downstream of the oxygenator. With this construction, the apparatus establishes a blood flow path from the blood inlet to the blood outlet. The blood flow path includes vortex flow in the de-aering region to separate air from blood, generally longitudinal flow from the de-aering region along the core, and generally radial flow from the core and through the heat exchanger and oxygenator, and to the outlet. The apparatus removes gross air from the blood flow at the de-aering region and thus prior to interaction with the heat exchanger and oxygenator.

BRIEF DESCRIPTION OF THE INVENTION

DETAILED DESCRIPTION

Figure 1A:
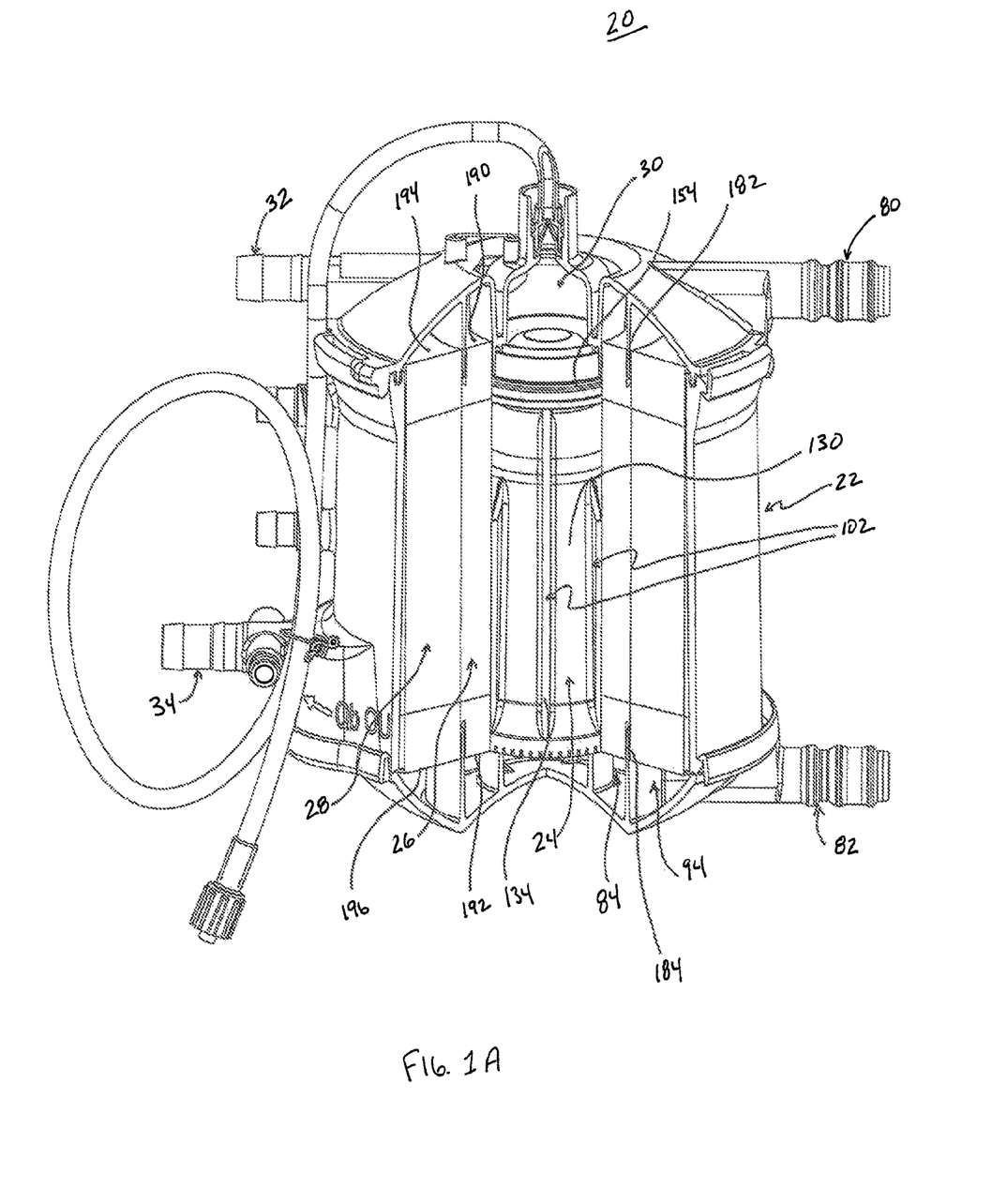
FIG. 1A is a perspective view of an apparatus in accordance with principles of the present disclosure, with portions cut away.
Figure 1B:
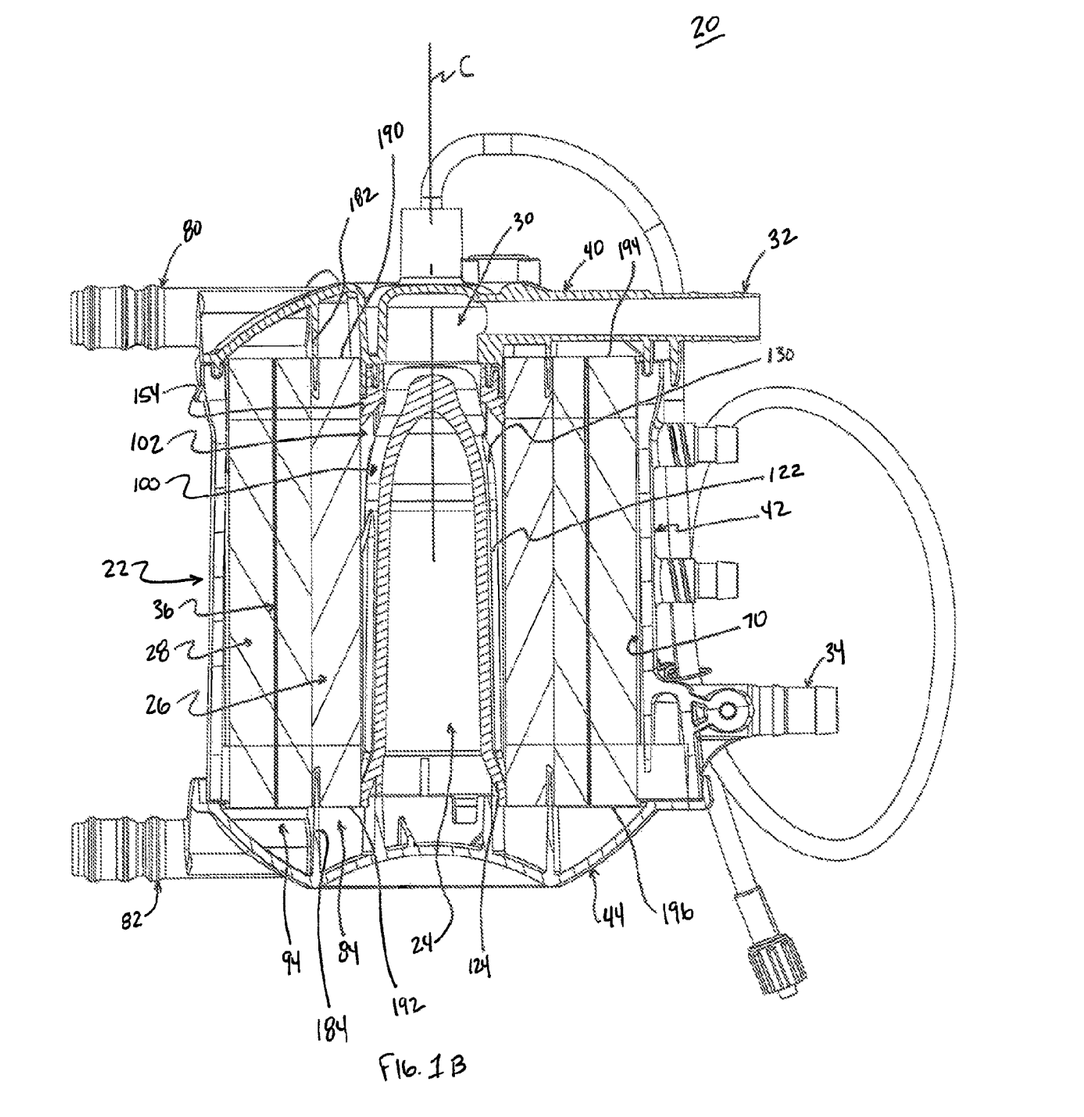
FIG. 1B is a cross-sectional view of the apparatus of FIG. 1A.

One embodiment of an apparatus 20 in accordance with principles of the present disclosure and useful for treating blood in an extracorporeal blood circuit is shown in FIGS. 1A and 1B. The apparatus includes a housing 22, a manifold body 24, a heat exchanger 26, and an oxygenator 28. Details on the various components are provided below. In general terms, however, a portion of the housing 22 (e.g., an upper end cap 40 shown in FIG. 2A and described below) and the manifold body 24 combine to form a de-aering region or bubble trap 30. A blood inlet 32 is arranged relative to the de-aering region 30 so as to direct incoming blood tangentially into the de-aering region 30. A blood outlet 34 is connected to the housing 22, downstream of the heat exchanger 26 and the oxygenator 28. A blood flow path is defined from the blood inlet 32 to the blood outlet 34, with gross air removal occurring within the de-aering region 30, and prior to interaction of the blood with the heat exchanger 26 or the oxygenator 28. The apparatus 20 thus performs gross air removal, temperature control, and oxygenation of the patient's blood (as part of an extracorporeal blood circuit) with minimal impact on the circuit's overall prime volume. Optionally, the apparatus 20 can further include a filter media 36 (referenced generally in FIG. 1B) akin to an arterial filter media downstream of the de-aering region 30 for trapping GME and/or particulates. As a point of reference, "gross air" removal at the de-aering region 30 is understood by those of ordinary skill in the art to generally include relatively large volume air bubbles that would otherwise simulate a CVR draining. In some embodiments, gross air removal can be estimated by injecting a 30 cc bolus of air into the apparatus 20 and measuring whether any air comes out of the apparatus 20. In alternative embodiments, apparatuses in accordance with principles of the present disclosure omit one or both of the heat exchanger 26 and/or the oxygenator 28.

Figure 2A:
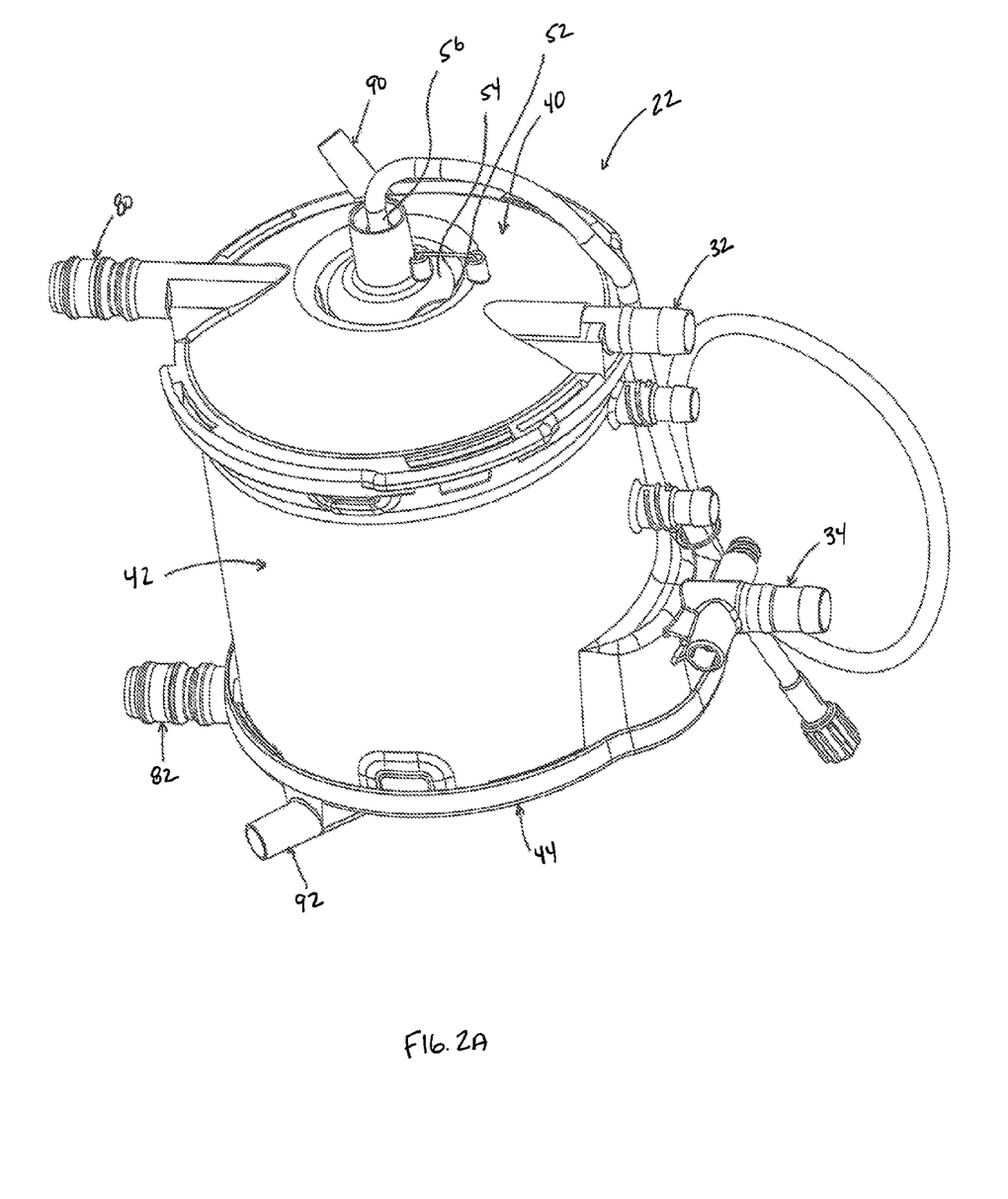
FIG. 2A is a perspective view of a housing component of the apparatus of FIG. 1A.
Figure 2B:
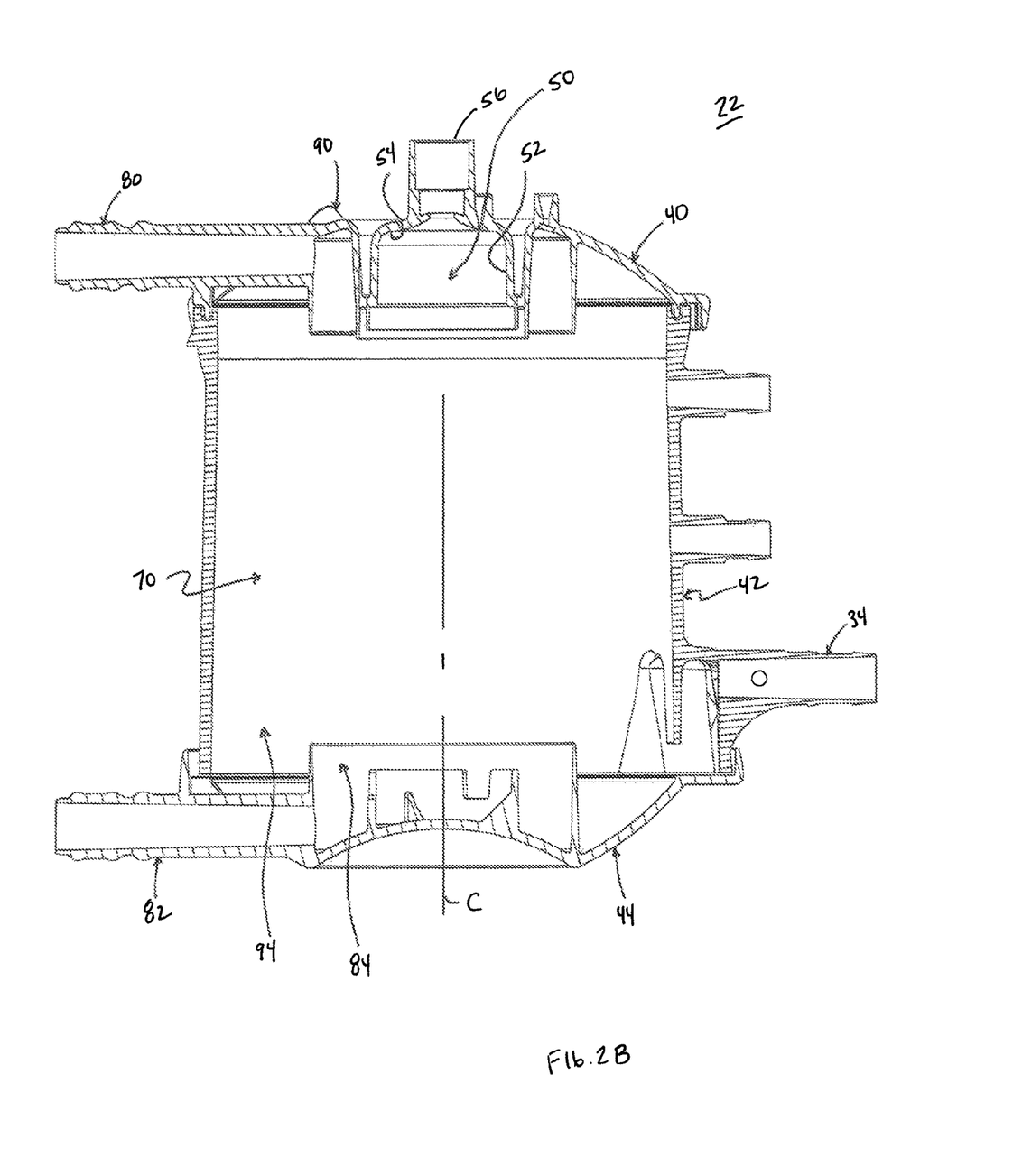
FIG. 2B is a cross-sectional view of the housing of FIG. 2A.

One embodiment of the housing 22 is shown in greater detail in FIGS. 2A and 2B, and can assume a variety of forms.

The housing 22 can include various components separately formed and subsequently assembled to one another, such as a first or upper end cap 40, a central portion 42, and a second or lower end cap 44. The end caps 40, 44 are configured for assembly to opposing ends of the central portion 42 as shown. In other constructions, the central portion 42 is integrally formed with one or both of the end caps 40, 44. The housing 22 can be made of a transparent medical grade material, such as a transparent polycarbonate, so that a user is able to observe the flow of blood through the apparatus 20 (FIG. 1A).

The first end cap 40 can incorporate various features, and generally defines a first chamber 50 via a side wall 52 (shown best in FIG. 2B). A cylindrical shape of the side wall 52 defines a central axis C of the first chamber 50. The first chamber 50 serves as part of the de-aering region 30 (FIGS. 1A and 1B) as described below, and the side wall 52 can have a substantially uniform diameter (e.g., within 5° of a true uniform diameter) in longitudinal or axial extension along the central axis C. The first chamber 50 is further defined by a top wall 54, with an air purge port 56 formed at or by the top wall 54 being fluidly open to the first chamber 50.

Figure 2C:
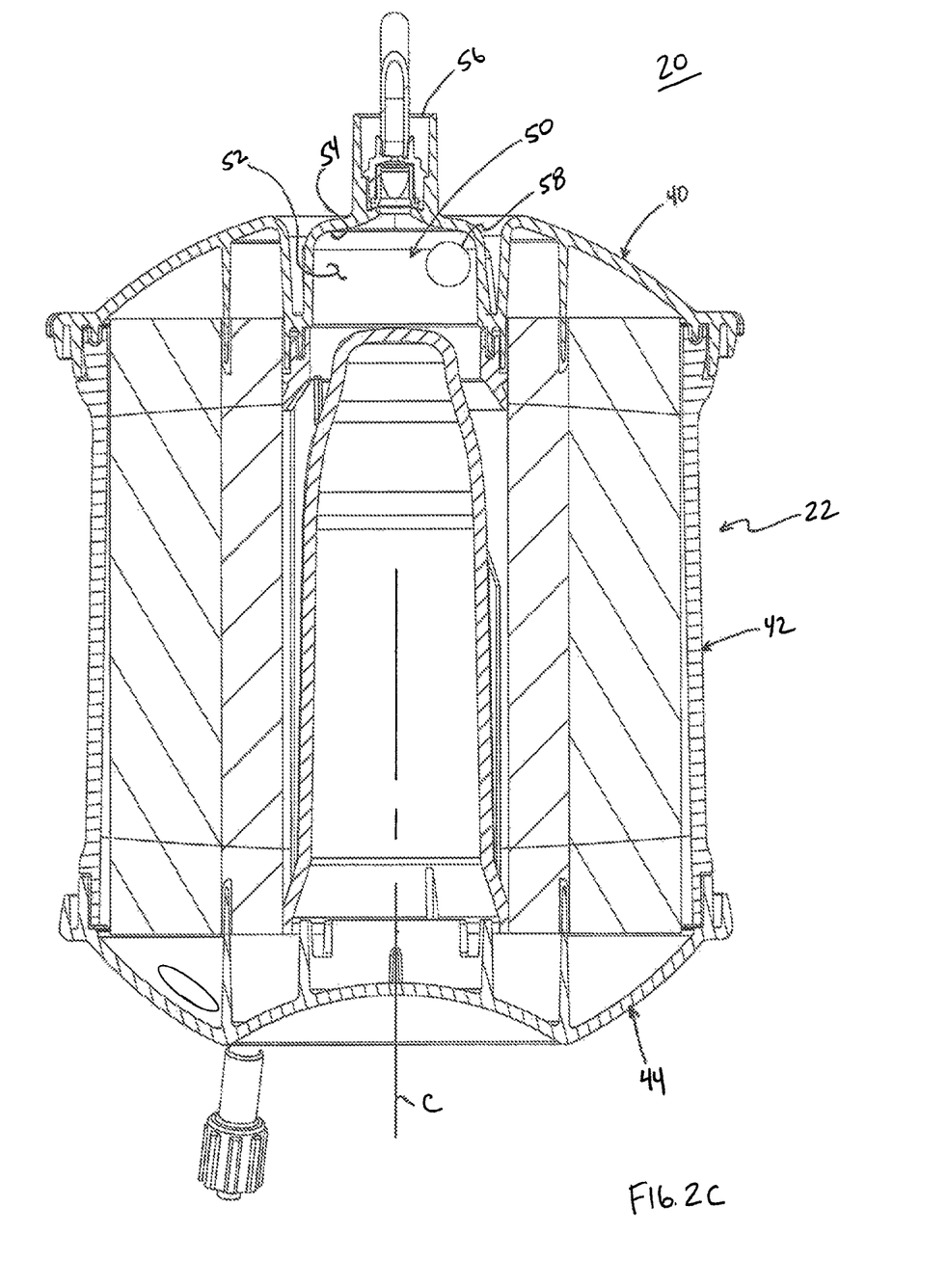
FIG. 2C is a cross-sectional view of the apparatus of FIG. 1A.

As reflected in FIG. 2A, the blood inlet 32 is integrally formed by the first end cap 40. Alternatively, the blood inlet 32 can be separately formed, and subsequently assembled to, the first end cap 40. Regardless, the blood inlet 32 is fluidly open to the first chamber 50 at an opening 58 in the side wall 52 as best shown in FIG. 2C. To this end, the blood inlet 32 (FIG. 2A) is arranged such that the opening 58 opens tangentially along a horizontal plane (i.e., perpendicular to the central axis C) into the first chamber 50. With this construction, the blood inlet 32 directs incoming blood substantially tangentially into the first chamber 50, and is sized, relative to the expected volume and flow rate of incoming blood, to produce a rotational flow along the side wall 52, and in particular a vortex flow. Stated otherwise, the blood inlet 32 is located so that it extends over a tangent to the side wall 52, and thereby delivers incoming blood off the central axis C of the first chamber 50 and directly to the side wall 52 substantially tangentially thereto (i.e., within 5° of a true tangential relationship). Due to the substantially tangential delivery of the incoming blood, the incoming blood is set in the interior of the first chamber 50 into a rotational motion.

The central portion 42 has a substantially cylindrical shape, and when assembled to the first end cap 40, generally defines a second chamber 70 as best shown in FIG. 2B. The first chamber 50 is fluidly open to the second chamber 70, with the second chamber 70 having an enlarged volume as compared to that of the first chamber 50. The cylindrical shape establishes a central axis of the central portion 42 that is, in some embodiments, co-axial with the first chamber central axis C. The blood outlet 34 is formed by or assembled to the central portion 42, and is fluidly open to the second chamber 70. In this regard, the blood outlet 34 extends radially relative to the central axis C in some embodiments.

The second end cap 44 can assume various forms, and is generally constructed so as to close the second chamber 70 opposite the first end cap 40.

As reflected in FIGS. 2A and 2B, the housing 22 can form or carry other ports in addition to the blood inlet 32, the blood outlet 34, and the air purge port 56. For example, a heat exchange inlet and outlet 80, 82 are formed or carried by the first and second end caps 40, 44, respectively. As described below, the heat exchange inlet and outlet 80, 82 are fluidly connected to a heat exchange zone 84 generally defined by the housing 22. Similarly, an oxygen fluid inlet 90 and an oxygen fluid outlet 92 are formed by the first end cap 40 and the second end cap 44, respectively. As described below, the oxygen fluid inlet and outlet 90, 92 are fluidly open to an oxygenating zone 94 generally defined by the housing 22. The inlets 80, 90 and the outlets 82, 92 can alternatively be located at other locations along the housing 22.

Figure 3A:
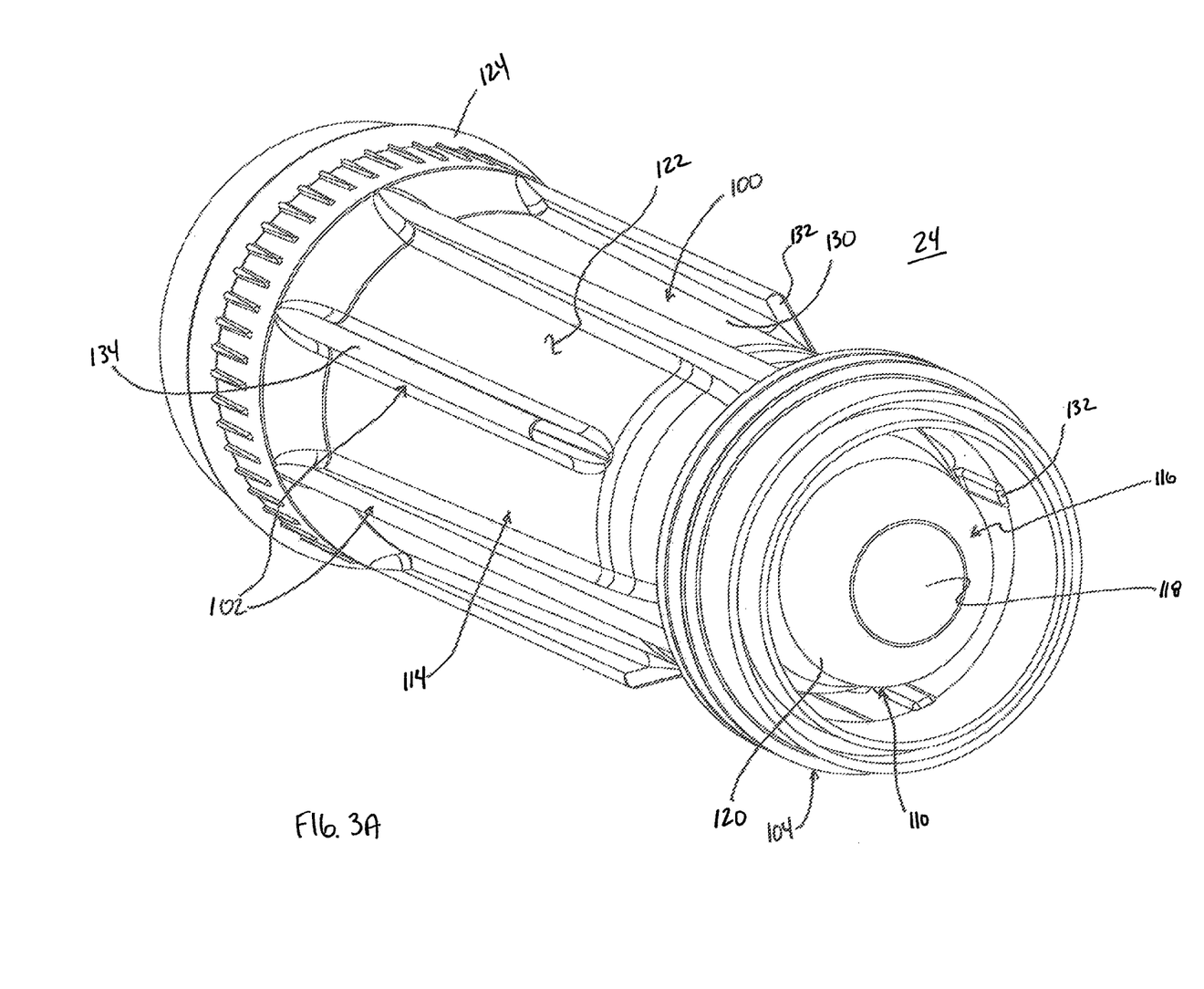
FIG. 3A is a perspective view of a manifold body component of the apparatus of FIG. 1A.
Figure 3B:
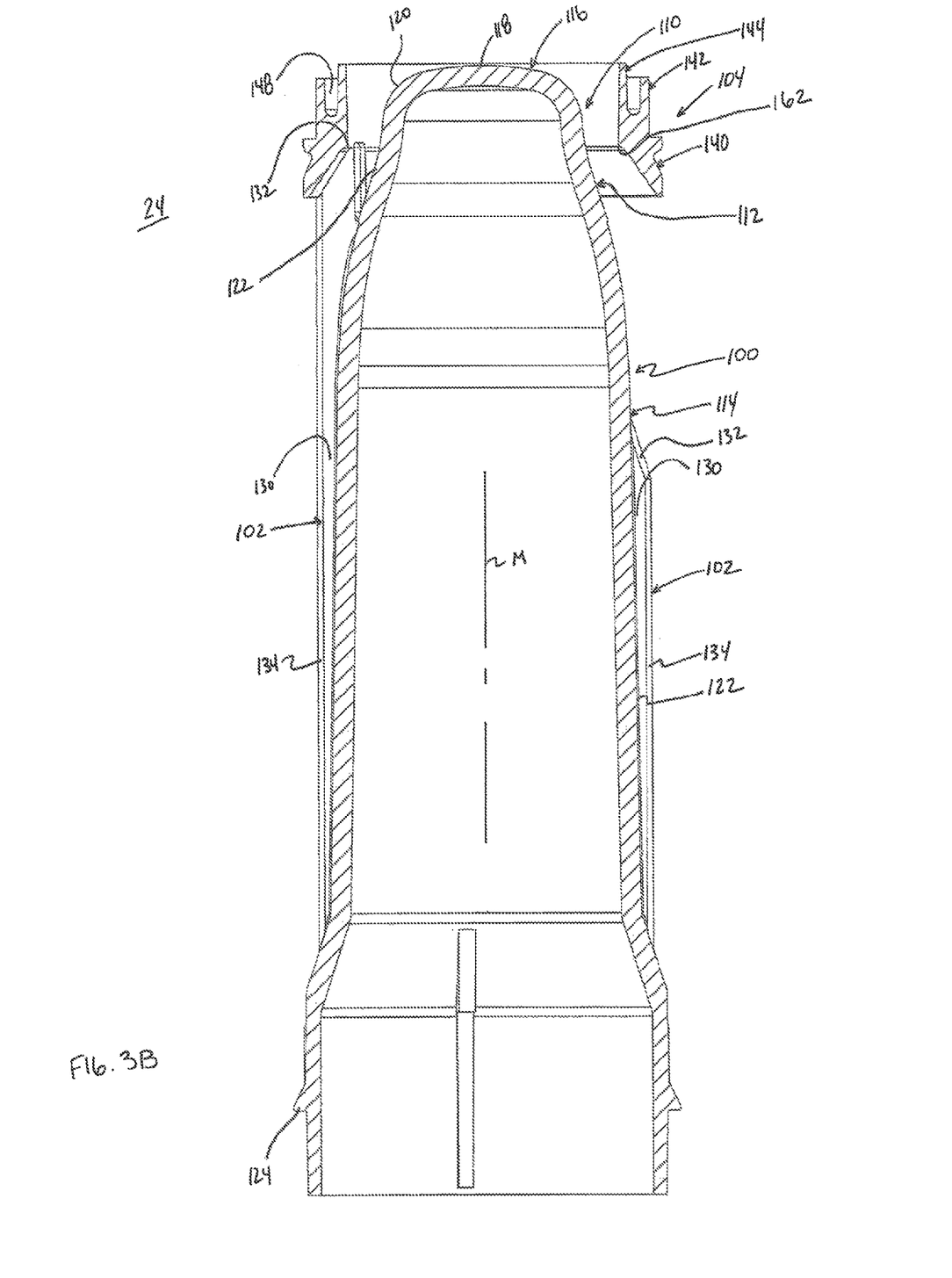
FIG. 3B is a simplified cross-sectional view of a portion of the manifold body of FIG. 3A.

Returning to FIGS. 1A and 1B, the manifold body 24 is configured for assembly within the housing 22, arranged co-axially with the central axis C. With reference to FIGS. 3A and 3B, the manifold body 24 includes or defines a core 100 forming a central axis M, a plurality of vanes or ribs 102, and a hub structure 104. The vanes 102 extend longitudinally (i.e., in a direction generally parallel with the central axis M) along the core 100, and serve to direct blood flow in a desired fashion as described below. The hub structure 104 facilitates assembly of the manifold body 24 to the first end cap 40 (FIG. 1B), and effectuates desired volume displacement in combination with various surface features of the core 100. The manifold body 24 can be a homogenous structure, for example an injection molded, medical grade plastic.

The core 100 includes or defines a head segment 110, a neck segment 112, and a base segment 114. An exterior of the head segment 110 terminates at a top surface 116 defining a center region 118 and curved outer region 120. The center region 118 can be planar 118 as generally reflected by FIG. 3B, or can be curved (e.g., the center region 118 and the outer region 120 combine to define a continuous curve at the top of the core 100). The outer region 120 forms a smooth curvature from the center region 118 to an outer longitudinal surface 122 of the core 100. The outer longitudinal surface 122 is continuous along the head segment 110, the neck segment 112, and the base segment 114 (as reflected for example, in FIGS. 3A and 3B in which element number 122 is shown as referencing differing locations along the core 100). In this regard, a diameter of the outer longitudinal surface 122 along the head segment 110 is substantially uniform (e.g., within 5° of a true uniform diameter) in longitudinal extension from the curved outer region 120 to the neck segment 112. For reasons made clear below, the outer diameter of the head segment 110 is less than a diameter of the first chamber side wall 52 (FIG. 2B).

The outer longitudinal surface 122 exhibits an expanding outer diameter along the neck segment 112 in longitudinal extension from the head segment 110 to the base segment 114. The base segment 114 also expands in outer diameter from the neck segment 112 to a lower mounting ledge 124. However, the taper in diameter along the neck segment 112 is greater than that of the base segment 114. Stated otherwise, relative to the manifold central axis M, a slope defined by the outer surface 122 along the neck segment 112 is greater than a slope defined along the base segment 114.

The vanes 102 can be identical, and are circumferentially spaced from one another about a perimeter of the core outer surface 122. The vanes 102 and the outer surface 122 of the core 100 combine to define a plurality of axial channels or grooves 130 (best illustrated in FIGS. 1A and 3A). Relative to a longitudinal direction (i.e., parallel with the manifold central axis M), the vanes 102 extend from the mounting ledge 124 along the base segment 114, the neck segment 112, and a portion of the head segment 110. As best shown in FIG. 3B, each of the vanes 102 terminates at an end point 132 that is longitudinally offset from the top surface 116. That is to say, the top surface 116, and in particular the curved outer region 120, is free of the vanes 102, providing a smooth transition for blood flow to the channels 130. In other embodiments, the vanes 102 can extend to the top surface 116. A radial component (i.e., perpendicular to the manifold central axis M) of the vanes 102 in projection from the outer surface 122 generates a longitudinal edge 134 opposite the core 100. The edge 134 is substantially parallel with the manifold central axis M between the hub structure 104 and the mounting ledge 124. Thus, the edges 134 collectively define a substantially uniform diameter between the hub structure 104 and the mounting ledge 124.

The hub structure 104 is connected to the vanes 102 adjacent the head 110. The hub structure 104 can incorporate various features for assembling the manifold body 24 with the first end cap 40 (FIG. 1B). For example and with reference to FIGS. 3B and 4, the hub structure 104 can form outer, intermediate and inner rings 140-144. The intermediate ring 142 is sized and shaped for sealed assembly within an annular slot 146 formed by the first end cap 40. Similarly, an annular groove 148 formed between the intermediate and inner rings 142, 144 is sized to sealingly receive a circular projection 150 of the first end cap 40. Other mounting constructions are also envisioned. With the one embodiment illustrated, however, the outer ring 140 combines with an annular partition 152 of the first end cap 40 to define a relatively continuous support surface 154 configured to receive and support a portion of the heat exchanger 26 (FIG. 1A) as described below. As shown, a diameter of the outer ring 140, and thus of the support surface 154, is commensurate with the diameter collectively defined by the vanes 102.

Regardless of the exact features provided with the hub structure 104 for assembly to the first end cap 40 (FIG. 1B), the inner ring 144 is provided. The inner ring 144 surrounds, but is radially offset from, the head segment 110. As shown, a leading end 160 of the inner ring 144 is generally aligned with the top surface 116 for reducing a prime volume of the resultant apparatus 20 (FIG. 1A). In other embodiments, the leading end 160 can be longitudinally offset from the top surface 116 without affecting functionality of the resultant apparatus 20. A trailing end 162 of the inner ring 144 is located above the neck segment 112. Relative to an upright orientation, then, the inner ring 144 extends longitudinally above or beyond the end point 132 of each of the vanes 102. Further, the inner ring 144 defines a diameter commensurate with a diameter of the first chamber side wall 52 as shown in FIG. 4.

Figure 4:
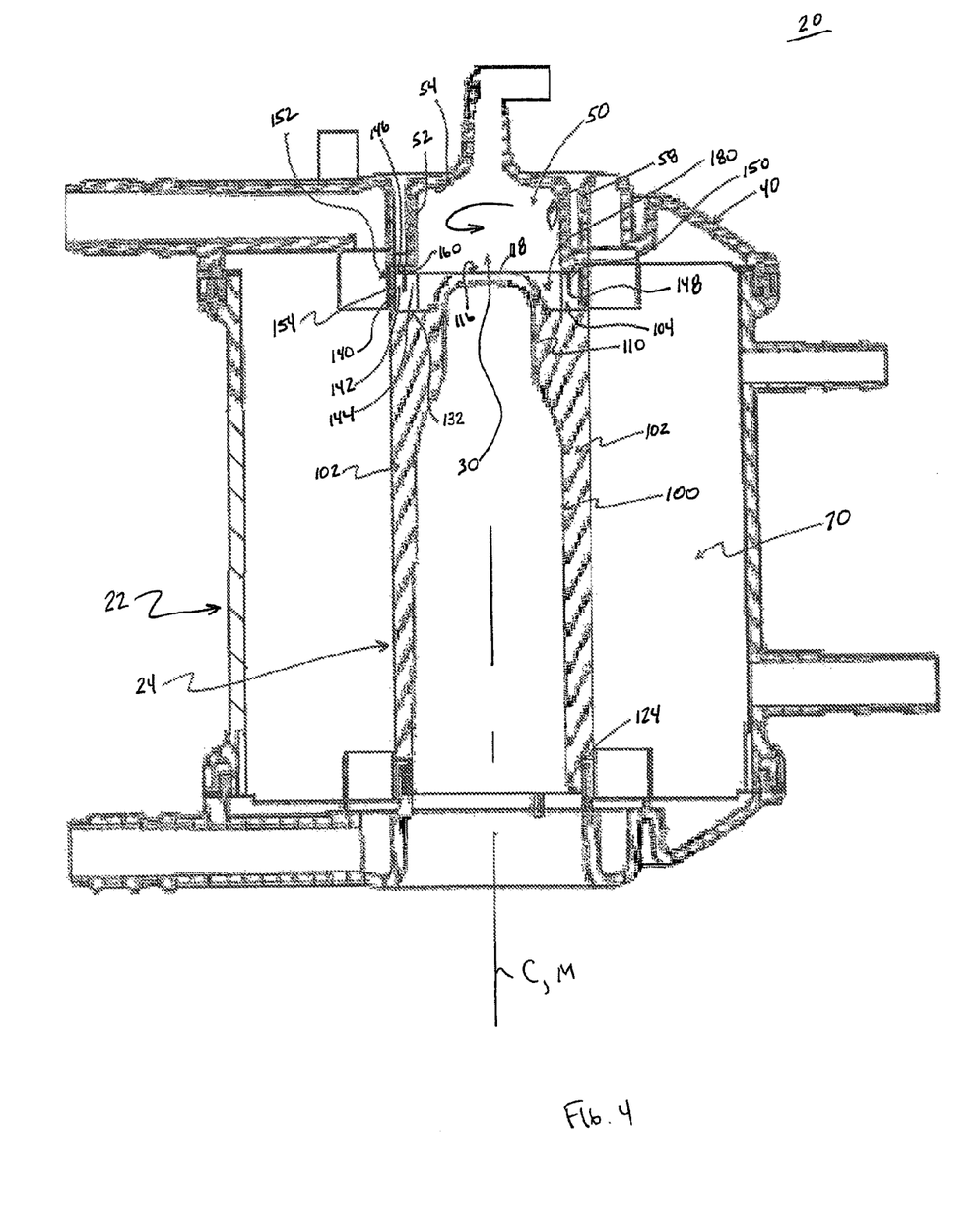
FIG. 4 is a cross-sectional view illustrating assembly of the manifold body of FIG. 3A within the housing of FIG. 2A.

As shown in FIG. 4, upon final assembly the manifold body 24 combines with the housing 22 to establish the de-aering zone 30 at the first chamber 50. As a point of reference, FIG. 4 reflects the co-axial arrangement of the first chamber and manifold axes C, M. The de-aering region 30 is circumferentially bounded by the first chamber side wall 52. The top surface 116 of the head segment 110 defines a lower boundary (along the central axis C) of the de-aering region 30, whereas the first chamber top wall 54 serves as an upper boundary. A desired vortex flow of incoming blood (represented by an arrow in FIG. 4) is readily formed within the de-aering region 30 due to the tangential entry of the blood and presence of the head segment 110. An effective height of the core 100 (i.e., longitudinal distance between the planar center region 118 and the mounting ledge 124) is sized in accordance with a height of the housing 22. More particularly, the manifold body 24 is configured such that upon final assembly within the housing 22, the head segment 110 is aligned with the first chamber 50, and the top surface 116/center region 118 is longitudinally offset (or below relative to the orientation of FIG. 4) from the blood inlet 32 (FIG. 1B), and in particular the inlet opening 58 in the side wall 52. With this construction, incoming blood otherwise caused to rotate within the first chamber 50 "sits" on the top surface 116, with the center region 118 effectively serving as a low pressure support surface. The head segment 110 is thus offset (i.e., below) from the rotating flow, such that the desired vortex flow is not impeded.

A volume displacement region 180 (referenced generally) is established by the core 100 immediately below, and fluidly open to, the de-aering region 30. The volume displacement region 180 is akin to an annular ring and directs blood flow from the de-aering region 30 to the channels 130 (FIG. 1A) as described below, through an annular gap between the head segment 110 and the inner ring 144. The volume displacement region 180 is co-axial with the central axis C, the annular gap between the head segment 110 and the inner ring 144, and the de-aering zone 30. The channels 130, in turn, guide blood flow from the volume displacement region 180 to the second chamber 70 as described below.

Returning to FIGS. 1A and 1B, the heat exchanger 26 includes a bundle or plurality of hollow, heat transfer elements, which may be fibers, tubes, capillaries, compartments, etc. (not shown individually). In some embodiments, the heat transfer elements comprise a thermally conductive polymer or metal. Various shapes of heat transfer elements are contemplated by the present disclosure. One exemplary material for the heat exchanger capillaries is polyethylene terephthalate, for example HEX PET™ heat exchange capillary. The HEX PET pre-made mat generally comprises two layers of hollow capillaries, within the two layers being angled with respect to one another (e.g., a 15 degree angle or bias from normal). Other materials are also envisioned. In general terms, the purpose of the heat transfer elements of the heat exchanger 26 is to transfer heat to or from the exchange fluid running therethrough to or from the blood that flows between the heat transfer elements.

The heat transfer elements of the heat exchanger 26 are located around the manifold body 24 (and thus within the second chamber 70), and may be tightly wound or wrapped concentrically about the manifold body 24. Also, the heat transfer elements may be located such that there is minimal or no structural obstruction between the manifold body 24 and the heat exchanger 26. In this regard, the heat transfer elements of the heat exchanger 26 contact or bear against the edge 134 of each of the vanes 102, as well as the support surface 154. Thus, and as best shown in FIG. 1B, while the heat transfer elements of the heat exchanger 26 do not contact the outer longitudinal surface 122 of the core 100, the channels 130 are fluidly open to the heat transfer elements such that blood flow along the channels 130 is directed into (or between) the heat transfer elements. Alternatively to the heat transfer elements actually being wound on the manifold body 24, the heat exchanger 26 can comprise heat transfer elements that are pre-arranged in a woven mat or fabric-like arrangement that is assembled over the vanes 102.

The heat exchanger 26 may either heat or cool the blood flowing through the apparatus 20. Since hypothermia may be used during cardiac surgery (especially in infant and pediatric surgeries), to reduce oxygen demand, and since rapid re-warming of the blood can produce bubble emboli, the heat exchanger 26 is generally used to gradually re-warm blood and prevent emboli formation. The exchange or heat transfer fluid used in the heat exchanger 26 may comprise water or other suitable fluids. The heat exchanger 26 may incorporate hot and cold tap water that is run through the plurality of heat transfer elements. In some embodiments, however, a separate heater/cooler unit (not shown) with temperature-regulating controls is used to heat or cool the exchange fluid outside of the apparatus 20 as necessary to regulate the temperature of the blood flowing between the heat transfer elements as desired. As another alternative, a heat transfer means other than a fluid is possible. For example, thermoenergy may be supplied to the heat transfer elements rather than a fluid. As generally reflected in FIG. 1B, the heat exchanger 26 is sized and shaped for assembly within the heat exchange zone 84 (e.g., defined by dividers 182, 184 formed by the end caps 40, 44, respectively), and can incorporate bands and/or a potting compound (as known in the art) to effectuate sealed, fluid communication between opposing ends 190, 192 (referenced generally) of the heat transfer elements and the heat exchange inlet and outlet 80, 82.

The oxygenator 28 is generally disposed about the heat exchanger 26 (and thus within the second chamber 70), and includes a plurality of gas exchange elements (not individually shown). A bundle or plurality of hollow fibers are used for gas exchange and are made of semi-permeable membrane including micopores. In some embodiments, the gas exchange elements are hollow polypropylene fibers, but other materials are also contemplated by the present disclosure. Any suitable microporous fiber maybe used as the gas exchange elements of the oxygenator 28. The gas exchange elements (or fibers) of the oxygenator 28 are arranged around the heat exchanger 26, and in a generally cylindrical shape. The hollow fibers of the oxygenator 28 can be wound directly on the heat exchanger 26, for example as described in U.S. Pat. No. 5,346,612, the entire teachings of which are incorporated herein by reference. For example, one long microporous fiber may be wound back and forth on the heat exchanger 26. After winding, the fiber is cut at a plurality of locations that are located near opposing ends 194, 196 (referenced generally) that will allow a gas medium to enter the cut segments of the fiber. Alternatively, the oxygenator 28 can optionally be formed by following a method of helically winding continuous, semi-permeable, hollow fiber on some intermediary component, rather than directly on the heat exchanger 26. As known to those of skill in the art, the winding angle and/or tension during the winding process can be manipulated to affect a variable packing fraction as desired. One example pattern of winding the fibers of the oxygenator 28 is found on the Affinity™ oxygenator available from Medtronic, Inc., of Minneapolis, Minn. Regardless of an exact construction, the oxygenator 28 is sized and shaped for assembly within the oxygenating zone 94 (e.g., defined by the dividers 182, 184 and the central portion 42), and can include bands or a potting compound (as is known in the art) to effectuate sealed, fluid communication of the gas transfer element ends 194, 196 with the oxygenator inlet and outlet 90, 92 (FIG. 2A).

An oxygen-containing gas medium is provided through the plurality of gas exchange elements of the oxygenator 28. Certain gases are able to permeate the fibers. Carbon dioxide from the blood surrounding the fibers diffuses through the walls of the fibers and into the gas mixture. Similarly, oxygen from the gas mixture inside the fibers diffuses through the micropores into the blood. The gas mixture then has an elevated carbon dioxide content and preferably exits the opposite ends of the fibers as it moves out of the apparatus 20 via the oxygen outlet 92 (FIG. 2A). Although oxygen and carbon dioxide are preferably being exchanged, as described above, the present disclosure also contemplates that other gases may be desired to be transferred.

Any suitable gas supply system may be used with the oxygenator 28. For example, the gas supply system may include flow regulators, flow meters, a gas blender, an oxygen analyzer, a gas filter, and a moisture trap. Other alternative or additional components in the gas supply system can be included.

In addition to the de-aering zone 30, the heat exchanger 26, and the oxygenator 28, the apparatus 20 can optionally include other blood treatment components. For example, the apparatus 20 can optionally include the filter media 36 (drawn generally in FIG. 1B). The filter media 36 is akin to conventional arterial filter filtration materials, and is constructed to trap or capture GME and small particles contained in blood passing through the filter media 36. The filter media 36 can be located at various locations within the apparatus 20. In one embodiment, the filter media 36 can be located around gas exchange elements of the oxygenator 28. Alternatively, the filter media 36 can be arranged between the heat exchanger 26 and the oxygenator 28. Yet another possibility is for the filter media 36 to be located in between layers of the wound fibers or gas exchange elements of the oxygenator 28. For example, during winding of gas exchange elements or fibers comprising the oxygenator 28, the winding is interrupted and the filter media 36 is placed around the so-wound fibers or gas exchange elements, and the winding is continued to complete the oxygenator 28. An advantage of locating the filter media 36 within the oxygenator 28 is that blood running between the gas exchange elements of the oxygenator 28 is oxygenated, then filtered, and then oxygenated again after filtering, thereby bringing the level of oxygen in the blood up to a desired level after filtration. Other configurations or designs of the apparatus 20 including the optional filter media 36 are contemplated by the present disclosure and are not limited to those described herein. In yet other embodiments, the filter media 36 can be omitted.

Figure 5:
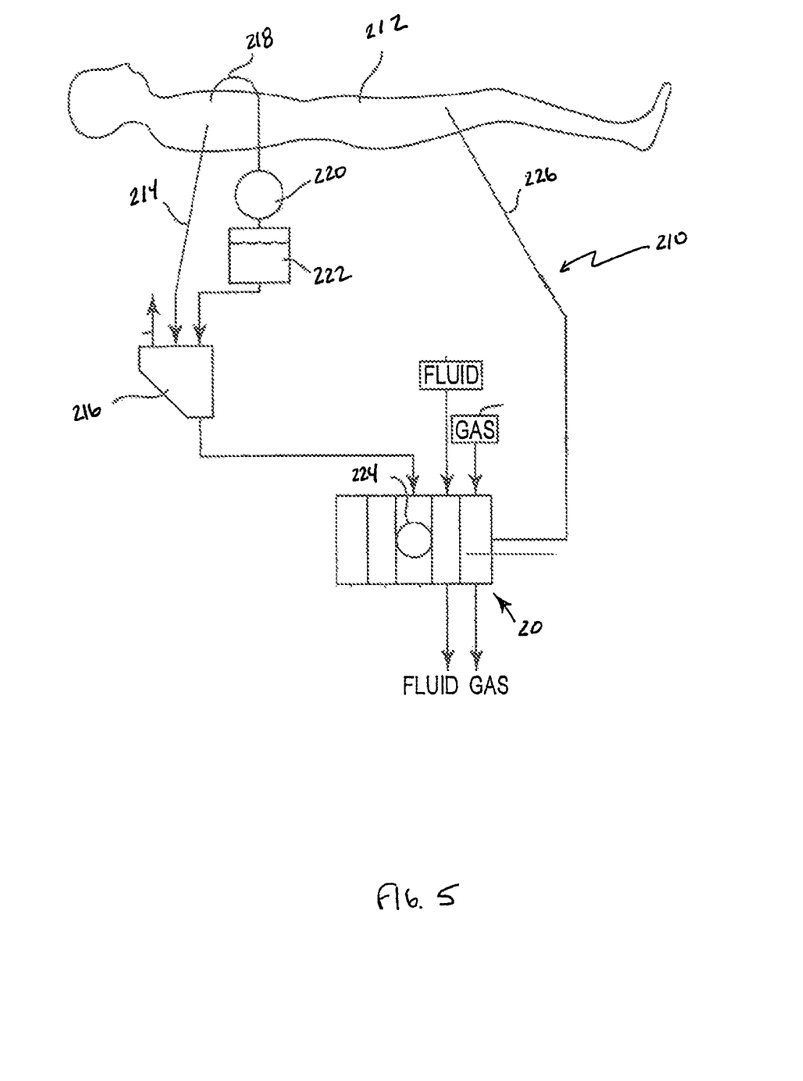
FIG. 5 is a schematic drawing of a cardiopulmonary bypass circuit including the apparatus of FIG. 1A.

The apparatus 20 may be used or incorporated into any appropriate system or device in which blood is desired to be oxygenated and temperature-controlled. One particular system is an electromechanical extracorporeal circulatory support system known as a cardiopulmonary bypass (CPB) system, commercially sold by Medtronic, Inc., of Minneapolis, Minn., under the trade name Performer-CPB System. Other systems are contemplated by the present disclosure. With this in mind, FIG. 5 provides an exemplary extracorporeal blood circuit 210 that includes the apparatus 20. The circuit 210 generally draws blood of a patient 212 during cardiovascular surgery through a venous line 214. Venous blood drawn from the patient 212 is discharged into a venous reservoir 216. Cardiotomy blood and surgical field debris are aspirated by a suction device 218 and are pumped by a pump 220 into a cardiotomy reservoir 222. Once defoamed and filtered, the cardiotomy blood is also discharged into the venous reservoir 216. Alternatively, the function of the cardiotomy reservoir 222 may be integrated into the venous reservoir 216. In the venous reservoir 216, air entrapped in the venous blood rises to the surface of the blood and is vented to the atmosphere.

A pump 224 draws blood from the venous reservoir 216 and pumps it through the apparatus 20. Some exemplary types of pumps 224 include, but are not limited to, roller pumps and centrifugal pumps. The pump 224 may be external to the apparatus 20 as shown, or may alternatively be incorporated into the apparatus 20. As described below, the blood is de-aerated, temperature controlled, and oxygenated by the apparatus 20, and then returned to the patient 212 via an arterial line 226. With some embodiments of the present disclosure, the apparatus 20 provides necessary filtration (e.g., via the optional filter media 36 (FIG. 1B)), such that the circuit 210 does not include a separate arterial filter device as normally employed with most CPB systems. As a result, a prime volume of the circuit 210 is reduced as compared to conventional extracorporeal blood circuits.

Figure 6:
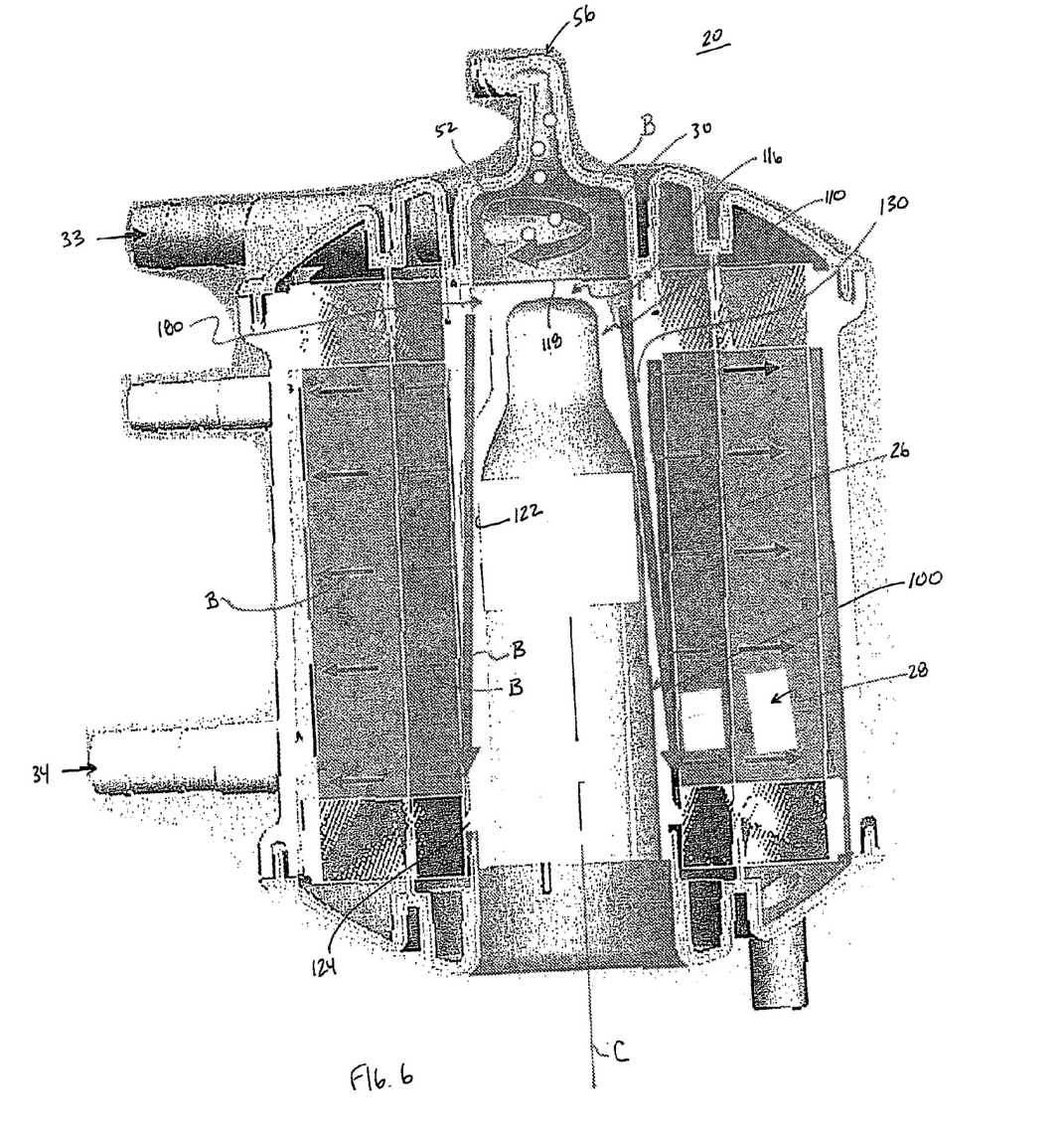
FIG. 6 is a cross-sectional side view of the apparatus of FIG. 1A showing blood flow through the apparatus.

Treatment and flow of blood within the apparatus 20 is reflected in FIG. 6. In general terms, a blood flow path (represented by arrows labeled B) is established from the blood inlet 32 to the blood outlet 34. Initially, the blood flow path includes a rotational or vortex flow within the de-aering region 30. As blood tangentially enters the de-aering zone 30, a swirling motion (vortexing) along the side wall 52 is induced about the first chamber central axis C, effectively "sitting" or residing on the planar central region 118 of the top surface 116. A pressure differential is thus created in the de-aering region 30, exhibiting an increasing pressure radially outward from the central axis C. The center region 118 supports the so-formed low pressure portion of the vortex flow. This pressure differential separates gross air from the incoming blood in the form of air bubbles. Due to the centrifugal force of the vortex flow, the air bubbles are forced to the central axis C and are relieved from the apparatus 20 via the air purge port 56. Thus, gross air removal (or de-aering) occurs prior to the blood encountering the heat exchanger 26 or the oxygenator 28.

The volume displacement or annular ring region 180 allows the rotating blood within the de-aering region 30 to flow, via gravity or pump pressure, toward the channels 130 (best shown in FIG. 1A). In this regard, the annular ring region 180 has a relatively uniform radial width and thus does not compress the blood flow. Blood flow to and along the channels 130 is substantially longitudinal (i.e., in the direction of the central axis C). The angle of the channels 130 (i.e., increasing outer diameter of the outer surface 122 in longitudinal extension from the head segment 110) is optimized to minimize the pressure drop in the blood flow longitudinally across the core 100. By tapering the core 100 outer diameter, a pressure at the volume displacement region 180 approximates a pressure at the mounting ledge 124. While traveling along the channels 130, the flow transitions from a substantially longitudinal direction to a substantially radial direction to and through the heat exchanger 26. In this regard, the blood flow is not subjected to compression or overt "turns" when traversing along the channels 130 and to the heat exchanger 26. The blood flow experiences a very low shear rate and thus minimal trauma.

The blood flows from the channels 130 in a substantially radial fashion (relative to the central axis C) between the heat exchange elements of the heat exchanger 26. A heat exchange fluid is forced through the heat exchange elements, effectuating transfer of heat with the blood in a desired direction. Substantially radial flow of the blood continues through the oxygenator 28, with the oxygenator 28 operating to oxygenate the blood. Where provided, the filter media 36 (FIG. 1B) interfaces with the radially flowing blood, and removes gaseous microembolisms and minute particles. Finally, the oxygenated and temperature-controlled blood flow exits the apparatus 20 via the blood outlet 34.

The oxygenating and temperature control apparatus of the present disclosure provide a marked improvement over previous designs. By de-aerating the blood prior to interfacing with the oxygenator, gross air bubbles are removed before being "chopped" up when traveling through the oxygenator (and the heat exchanger). Further, the blood flow experiences a minimal pressure drop in transitioning from the de-aering region 30 to the heat exchanger, thereby minimizing trauma. Finally, with embodiments in which the apparatus incorporates an arterial filter media, an overall prime volume of the corresponding extracorporeal blood circuit is reduced.

Although the present disclosure has been described with reference to preferred embodiments, workers skilled in the art will recognize that changes can be made in form and detail without departing from the spirit and scope of the present disclosure. For example, extracorporeal blood circuit apparatuses in accordance with principles of the present disclosure need not include one or both of the heat exchanger or the oxygenator components.

What is claimed is:

1. An apparatus for de-aering, oxygenating and controlling a temperature of blood in an extracorporeal blood circuit, the apparatus comprising:
   a housing generally defining a first chamber and a second chamber, the first chamber being fluidly open to the second chamber;
   a blood inlet fluidly open to the first chamber and arranged relative to a side wall of the first chamber to direct incoming blood tangentially into the first chamber;
   a manifold body disposed within the second chamber, the manifold body including a core forming a head and a plurality of vanes projecting from an outer surface of the core to define a plurality of channels, wherein the manifold body is arranged such that the head is aligned with the first chamber;
   a heat exchanger disposed within the second chamber and including a plurality of heat transfer elements arranged around the manifold body, wherein the channels are open to the heat exchanger;
   an oxygenator disposed within the second chamber and including a plurality of gas exchange elements arranged around the heat exchanger; and
   a blood outlet fluidly open to the second chamber;
   wherein the apparatus establishes a blood flow path from the blood inlet to the blood outlet, including rotational flow within the first chamber to separate air from the blood, generally longitudinal flow from the first chamber and along the channels, and generally radial flow through the second chamber.

2. The apparatus of claim 1, further comprising:
   an air purge port fluidly open to the first chamber for releasing air separated from blood within the first chamber.

3. The apparatus of claim 1, wherein the core is co-axially aligned with a central axis of the first chamber.

4. The apparatus of claim 3, wherein the rotational flow is about the central axis.

5. The apparatus of claim 3, wherein a top surface of the head combines with the side wall of the first chamber to form a de-aering region for the rotational flow.

6. The apparatus of claim 5, wherein the top surface is longitudinally spaced from the blood inlet.

7. The apparatus of claim 6, wherein relative to an upright orientation of the apparatus, the top surface is below the blood inlet.

8. The apparatus of claim 7, further comprising an air purge port fluidly open to the first chamber, wherein relative to the upright orientation, the air purge port is above the blood inlet.

9. The apparatus of claim 5, wherein the vanes extend along a portion of the head, terminating at a spatial location longitudinally offset from the top surface.

10. The apparatus of claim 1, wherein the manifold body further includes a ring longitudinally adjacent to and radially spaced from the head, the head and the ring combining to form a volume displacement region for directing blood flow from the first chamber to the channels.

11. The apparatus of claim 10, wherein an inner surface of the side wall of the first chamber defines a uniform diameter, and an inner diameter of the ring approximates the uniform diameter of the side wall.

12. The apparatus of claim 1, wherein the core further includes a neck extending from the head, and a base extending from the neck opposite the head, and further wherein the neck defines an increasing outer diameter in longitudinal extension from the head to the base.

13. The apparatus of claim 12, wherein at least a majority of the head defines a uniform outer diameter.

14. The apparatus of claim 13, wherein the vanes extend longitudinally along the base, the neck, and a portion of the head.

15. The apparatus of claim 1, wherein the heat exchanger contacts the vanes.

16. The apparatus of claim 1, further comprising:
a filter media disposed in the second chamber along the blood flow path.

17. The apparatus of claim 1, wherein the manifold body is configured to maintain a relatively uniform pressure in the blood flow from the first chamber along the channels.

18. An apparatus for de-aering, oxygenating and controlling a temperature of blood in an extracorporeal blood circuit, the apparatus comprising:
a housing defining a central axis;
a manifold body disposed within the housing and arranged co-axial with the central axis, the manifold body including a core;
wherein the housing and the manifold body combine to define a de-aering region having a cylindrical side wall and bounded along the central axis by a top wall and a low pressure support surface opposite the top wall;
a blood inlet fluidly open to the de-aering region and arranged relative to the side wall to direct incoming blood tangentially into the de-aering region, wherein the low pressure support surface is longitudinally offset from the blood inlet such that a vortex flow induced into the incoming blood is established on the low pressure support surface;
a heat exchanger disposed within the housing and including a plurality of heat transfer elements arranged around the manifold body;
an oxygenator disposed within the housing and including a plurality of gas exchange elements arranged around the heat exchanger;
a blood outlet fluidly open to an interior of the housing; and
a filter media disposed within the housing along the blood flow path
wherein the apparatus establishes a blood flow path from the blood inlet to the blood outlet, including vortex flow in the de-aering region to separate air from blood, substantially longitudinal flow from the de-aering region along the core, and generally radial flow from the core and through the heat exchanger and the oxygenator.

19. The apparatus of claim 18, further comprising:
an air purge port fluidly open to the de-aering region for releasing air separated from the blood within the de-aering region.

20. The apparatus of claim 18, wherein the manifold body further includes a plurality of vanes projecting from the core, the core and the vanes combining to define a plurality of channels for guiding blood flow from the de-aering region radially toward the heat exchanger.

21. The apparatus of claim 20, wherein the heat exchanger contacts the vanes.

22. A method of de-aering, oxygenating and controlling a temperature of blood within an extracorporeal blood circuit, the method comprising:
fluidly connecting a blood inlet and a blood outlet of an apparatus into an extracorporeal blood circuit, the apparatus including a housing forming a first chamber fluidly open to the blood inlet and a second chamber fluidly open to the first chamber, a manifold body including a central core forming a head and a plurality of vanes projecting from an outer surface of the core to define a plurality of channels, a heat exchanger including a plurality of heat transfer elements arranged around the manifold body such that the channels are open to the heat exchanger, and an oxygenator including a plurality of gas exchanging elements arranged around the heat exchanger;
delivering blood from the patient to the blood inlet;
establishing a vortex flow of the incoming blood in the first chamber to separate air from the incoming blood;
releasing the separated air from the apparatus;
directing the blood from the first chamber along the channels in a generally longitudinal direction;
directing the blood from the channels through the heat exchanger in a generally radial direction;
operating the heat exchanger to alter a temperature of the blood;
directing the blood from the heat exchanger through the oxygenator in a generally radial direction;
operating the oxygenator to oxygenate the blood; and
removing the blood from the apparatus via the outlet.

23. The method of claim 22, wherein establishing a vortex flow includes creating a low pressure zone in the first chamber above the head.

24. The method of claim 23, wherein the steps of directing the blood from the first chamber along the channels and through the heat exchanger includes maintaining a substantially constant pressure in the blood from the de-aering region to the heat exchanger.

* * * * *